United States Patent
Vega et al.

(10) Patent No.: US 8,138,387 B2
(45) Date of Patent: Mar. 20, 2012

(54) ABSORBENT ARTICLE WITH COLORED LOTIONED SHEET

(75) Inventors: Victor Nicholas Vega, Cincinnati, OH (US); Cornelia Beate Martynus, Nidderau-Ostheim (DE); Thomas James Klofta, Cincinnati, OH (US); Brandon Ellis Wise, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 161 days.

(21) Appl. No.: 12/121,358

(22) Filed: May 15, 2008

(65) Prior Publication Data

US 2008/0287903 A1 Nov. 20, 2008

(30) Foreign Application Priority Data

May 15, 2007 (EP) ..................................... 07108199
May 15, 2007 (EP) ..................................... 07108202

(51) Int. Cl.
*A61F 13/15* (2006.01)

(52) U.S. Cl. ........ 604/359; 604/361; 604/364; 604/367; 604/378; 604/385.06; 604/385.13; 604/385.24

(58) Field of Classification Search .................. 604/359, 604/361, 364, 367, 378, 385.01, 385.06, 604/385.13, 385.201, 385.24–385.3, 385.23
See application file for complete search history.

(56) References Cited

U.S. PATENT DOCUMENTS

| | | | |
|---|---|---|---|
| 1,926,900 A | 9/1933 | Haas | |
| 1,946,911 A | 2/1934 | Lindberg et al. | |
| 3,322,123 A | 5/1967 | Griswold et al. | |
| 3,489,148 A | 1/1970 | Duncan et al. | |
| 3,860,003 A | 1/1975 | Buell | |
| 4,253,461 A | 3/1981 | Strickland et al. | |
| 4,482,537 A * | 11/1984 | El-Menshawy et al. | 424/59 |
| 4,597,760 A | 7/1986 | Buell | |
| 4,597,761 A | 7/1986 | Buell | |
| 4,695,278 A | 9/1987 | Lawson | |
| 4,704,115 A | 11/1987 | Buell | |
| 4,738,676 A | 4/1988 | Osborn, III | |
| 4,795,454 A | 1/1989 | Dragoo | |
| 4,808,178 A | 2/1989 | Aziz et al. | |
| 4,909,802 A | 3/1990 | Ahr et al. | |
| 4,964,860 A | 10/1990 | Gipson et al. | |

(Continued)

FOREIGN PATENT DOCUMENTS

EP 1179329 A1 * 2/2002

(Continued)

OTHER PUBLICATIONS

PCT International Search Report, PCT/IB2008/051921 dated May 15, 2008.

(Continued)

*Primary Examiner* — Jacqueline F. Stephens
(74) *Attorney, Agent, or Firm* — Richard L. Alexander; Amy M. Foust

(57) ABSTRACT

An absorbent article to be worn by a wearer having a skin-contacting sheet such as a topsheet, a backsheet, an absorbent core and a colored hydrophilic lotion, that not only helps to reduce the adherence of the menses or feces to the skin, thereby improving the ease of menses or bowl movement (BM) clean up, but that also may serve as a wetness indicator. The absorbent articles may be infant (baby) diapers, including training pants, adult incontinence articles and the like.

11 Claims, 1 Drawing Sheet

U.S. PATENT DOCUMENTS

| | | | |
|---|---|---|---|
| 5,151,092 A | 9/1992 | Buell et al. | |
| 5,221,274 A | 6/1993 | Buell et al. | |
| 5,246,433 A | 9/1993 | Hasse et al. | |
| 5,318,774 A * | 6/1994 | Alban et al. | 424/59 |
| 5,431,643 A * | 7/1995 | Ouellette et al. | 604/385.05 |
| 5,460,805 A * | 10/1995 | Davis et al. | 424/69 |
| H1575 H * | 8/1996 | Daugherty et al. | 428/138 |
| 5,554,145 A | 9/1996 | Roe et al. | |
| 5,762,644 A | 6/1998 | Osborn, III et al. | |
| 5,827,917 A * | 10/1998 | Fourty | 524/451 |
| 5,830,487 A * | 11/1998 | Klofta et al. | 424/402 |
| D404,814 S | 1/1999 | Mayer | |
| 5,965,508 A * | 10/1999 | Ospinal et al. | 510/355 |
| 5,968,025 A | 10/1999 | Roe et al. | |
| 5,968,528 A * | 10/1999 | Deckner et al. | 424/401 |
| 6,042,842 A * | 3/2000 | Lemann et al. | 424/401 |
| 6,153,209 A * | 11/2000 | Vega et al. | 424/404 |
| 6,231,839 B1* | 5/2001 | Terren et al. | 424/60 |
| 6,270,486 B1 | 8/2001 | Brown et al. | |
| 6,372,202 B1* | 4/2002 | Simon | 424/63 |
| 6,403,107 B1* | 6/2002 | Lemann | 424/401 |
| 6,426,444 B2* | 7/2002 | Roe et al. | 604/364 |
| 6,482,191 B1 | 11/2002 | Roe et al. | |
| 6,515,029 B1 | 2/2003 | Krzysik et al. | |
| 6,570,055 B2 | 5/2003 | Yang et al. | |
| 6,689,932 B2 | 2/2004 | Kruchoski et al. | |
| 6,749,860 B2 | 6/2004 | Tyrrell et al. | |
| 6,756,520 B1 | 6/2004 | Krzysik et al. | |
| 7,158,269 B2 | 1/2007 | Morita | |
| 7,223,261 B2 | 5/2007 | Müeller et al. | |
| 7,273,476 B2 | 9/2007 | Mueller et al. | |
| 7,736,688 B2* | 6/2010 | Oetjen et al. | 427/2.1 |
| 7,771,735 B2 | 8/2010 | Dvoracek et al. | |
| 7,781,641 B2 | 8/2010 | Kasai | |
| 2002/0120241 A1 | 8/2002 | Tyrrell et al. | |
| 2003/0065299 A1* | 4/2003 | Carlucci et al. | 604/385.01 |
| 2003/0228339 A1* | 12/2003 | El-Nokaly et al. | 424/401 |
| 2004/0092900 A1 | 5/2004 | Hoffman et al. | |
| 2004/0092902 A1 | 5/2004 | Hoffman et al. | |
| 2005/0058669 A1* | 3/2005 | Krzysik et al. | 424/400 |
| 2005/0059941 A1 | 3/2005 | Baldwin et al. | |
| 2005/0095942 A1 | 5/2005 | Mueller et al. | |
| 2005/0196462 A1* | 9/2005 | Alimi | 424/600 |
| 2005/0276865 A1* | 12/2005 | Buyuktimkin et al. | 424/616 |
| 2006/0058765 A1 | 3/2006 | Mueller et al. | |
| 2006/0058766 A1 | 3/2006 | Mueller et al. | |
| 2006/0140924 A1 | 6/2006 | Schroeder et al. | |
| 2007/0233026 A1* | 10/2007 | Roe et al. | 604/361 |
| 2007/0286893 A1 | 12/2007 | Marsh et al. | |
| 2008/0193393 A1* | 8/2008 | Dayan | 424/59 |
| 2009/0137556 A1* | 5/2009 | Bonnichsen | 514/212.07 |

FOREIGN PATENT DOCUMENTS

| | | |
|---|---|---|
| EP | 1371379 A1 | 12/2003 |
| EP | 1444970 A1 | 8/2004 |
| EP | 1173231 B1 | 8/2005 |
| GB | 2263720 A | 8/1993 |
| WO | WO-92/11830 A2 | 7/1992 |
| WO | WO-97/05908 A2 | 2/1997 |
| WO | WO-97/05909 A2 | 2/1997 |
| WO | WO-98/29078 A1 | 7/1998 |
| WO | WO 9924010 A1 * | 5/1999 |
| WO | WO-99/45973 A1 | 9/1999 |
| WO | WO00/57843 | 10/2000 |
| WO | WO-00/64500 A1 | 11/2000 |
| WO | WO-00/64503 A1 | 11/2000 |
| WO | WO-00/74740 A1 | 12/2000 |
| WO | WO-02/34305 A2 | 5/2002 |
| WO | WO-02/49686 A2 | 6/2002 |
| WO | WO-02/070026 A1 | 9/2002 |
| WO | WO03/028776 | 4/2003 |
| WO | WO-03/057263 A1 | 7/2003 |
| WO | WO-2005/035013 A1 | 4/2005 |
| WO | WO-2006/022960 A1 | 3/2006 |
| WO | WO2007/105147 | 9/2007 |

OTHER PUBLICATIONS

U.S. Appl. No. 10/703,233, filed May 13, 2004, Hoffman, Anja et al.

* cited by examiner

ABSORBENT ARTICLE WITH COLORED LOTIONED SHEET

CROSS REFERENCE TO RELATED APPLICATION

This application claims priority to EPO Application No. 07108199.6, filed May 15, 2007, and EPO Application 07108202.8, filed May 15, 2007, the substances of which are incorporated herein by reference.

FIELD OF THE INVENTION

This invention is directed to an absorbent article to be worn by a wearer comprising a skin-contacting sheet, e.g. a topsheet, a backsheet and an absorbent core and thereon a colored hydrophilic lotion composition that reduces the adherence of the menses or feces to the skin (thereby improving the ease of menses or bowl movement (BM) clean up), said lotion composition comprising a coloring agent, giving the lotion composition a color, different to the color of the skin-contacting sheet. Absorbent articles may include infant (baby and toddler) diapers, including training pants; adult incontinence articles; feminine hygiene articles and the like.

BACKGROUND OF THE INVENTION

Disposable absorbent products, such as diapers and sanitary napkins, with a topsheet comprising a lotion are known in the art, for example to deliver skin benefits to the skin of the wearer. In recent years the focus has been to deliver lotions to sanitary napkins and diapers that provide extra skin benefits, for example by addition of botanical ingredients or pharmaceutical ingredients to the lotions. Lotions of various types are known to provide various skin benefits, such as prevention or treatment of diaper rash. These lotions can be applied to the topsheet of absorbent articles, and can be transferred to the skin of the wearer during use. U.S. Pat. No. 5,968,025 to Roe et al., WO 97/05908, WO 97/05909 and US 2006/140924 describe absorbent articles having lotioned topsheets for reducing adherence of BM to the skin, wherein the lotion compositions are primarily hydrophobic. U.S. Pat. No. 3,489,148 to Duncan et al. teaches a diaper comprising a hydrophobic and oleophobic topsheet wherein a portion of the topsheet is coated with a discontinuous film of oleaginous material. However, in diapers disclosed in the Duncan et al. reference and other diapers treated with hydrophobic lotions, the hydrophobic and oleophobic topsheets are relatively slow in promoting transfer of urine to the underlying absorbent cores.

However, there is an unmet need to provide absorbent articles to be worn by a wearer, such as diapers, sanitary napkins and the like, with some means to reduce the adherence of feces or menses to the skin. It is further desirable that removal of any feces or menses is improved after use of the article. Also, desired fluid acquisition and distribution properties should be maintained and wearer comfort should be ensured.

It has been found that when hydrophilic lotion compositions are provided, a reduction of the adherences of bodily exudates to the skin of the wearer can be achieved.

Furthermore, the inventors have now found that, unlike with the hydrophobic lotions of the prior art mentioned above, when a hydrophilic lotion composition is coloured by addition of a colouring agent, and applied on a surface of the absorbents article that may receive bodily exudates, the colouring agent migrates into the article upon such contact, e.g. wetting by BM, urine, blood. This may provide a signal to the user or care taker that the article may need changing. It may also provide a signal that the lotion composition is transferred to the skin.

SUMMARY OF THE INVENTION

Embodiments disclosed herein include an absorbent article to be worn by a wearer against the skin. The absorbent article comprises a backsheet, a skin contactable sheet, and an absorbent core. The skin-contactable sheet comprises a hydrophilic lotion composition containing a hydrophilic component and a coloring agent. The lotion composition has a water solubility of at least 30%. The lotion composition comprises 25% to 75% by weight of a first component which is liquid at 25° C. and 25% to 75% by weight of a second component which is solid at 25° C. The first component comprises one or more compounds selected from the group consisting of liquid nonionic surfactants having an HLB value greater than or equal to 10, liquid polyhydric alcoholic solvents, and liquid fatty acid esters comprising at least one fatty acid unit and at least one (poly) ethylene glycol unit and/or (poly) propylene glycol unit. The second component comprises one or more compounds selected from the group consisting of solid polypropylene glycols, solid polypropylene glycol derivatives, solid ethoxylated natural oils, solid ethoxylated natural fats, solid propoxylated natural oils, and solid propoxylated natural fats.

Embodiments disclosed herein also include an absorbent article comprising a skin-contactable sheet, wherein the skin-contactable sheet comprises a lotion composition. The lotion composition comprises 25% to 75% by weight of a first component which is liquid at 25° C., and 25% to 75% by weight of a second component which is solid at 25° C. The first component comprises one or more compounds selected from the group consisting of liquid nonionic surfactants having an HLB value greater than or equal to 10, liquid fatty acid esters comprising at least one fatty acid unit and at least one (poly) ethylene glycol unit, and liquid fatty acid esters comprising at least one fatty acid unit and at least one (poly) propylene glycol unit. The second component comprises one or more compounds selected from the group consisting of: (a) solid polyethylene glycols, solid polypropylene glycol, solid polyethylene glycol derivatives and/or solid polypropylene glycol derivatives; (b) solid nonionic surfactants with HLB value of at least 10; (c) solid fatty compounds selected from the group consisting of solid fatty acids, solid fatty soaps and solid fatty alcohols; and (d) ethoxylated natural oils and fats and propoxylated natural oils and fats. The first component and/or the second component also comprises a coloring agent

DETAILED DESCRIPTION OF THE INVENTION

Figure 1:
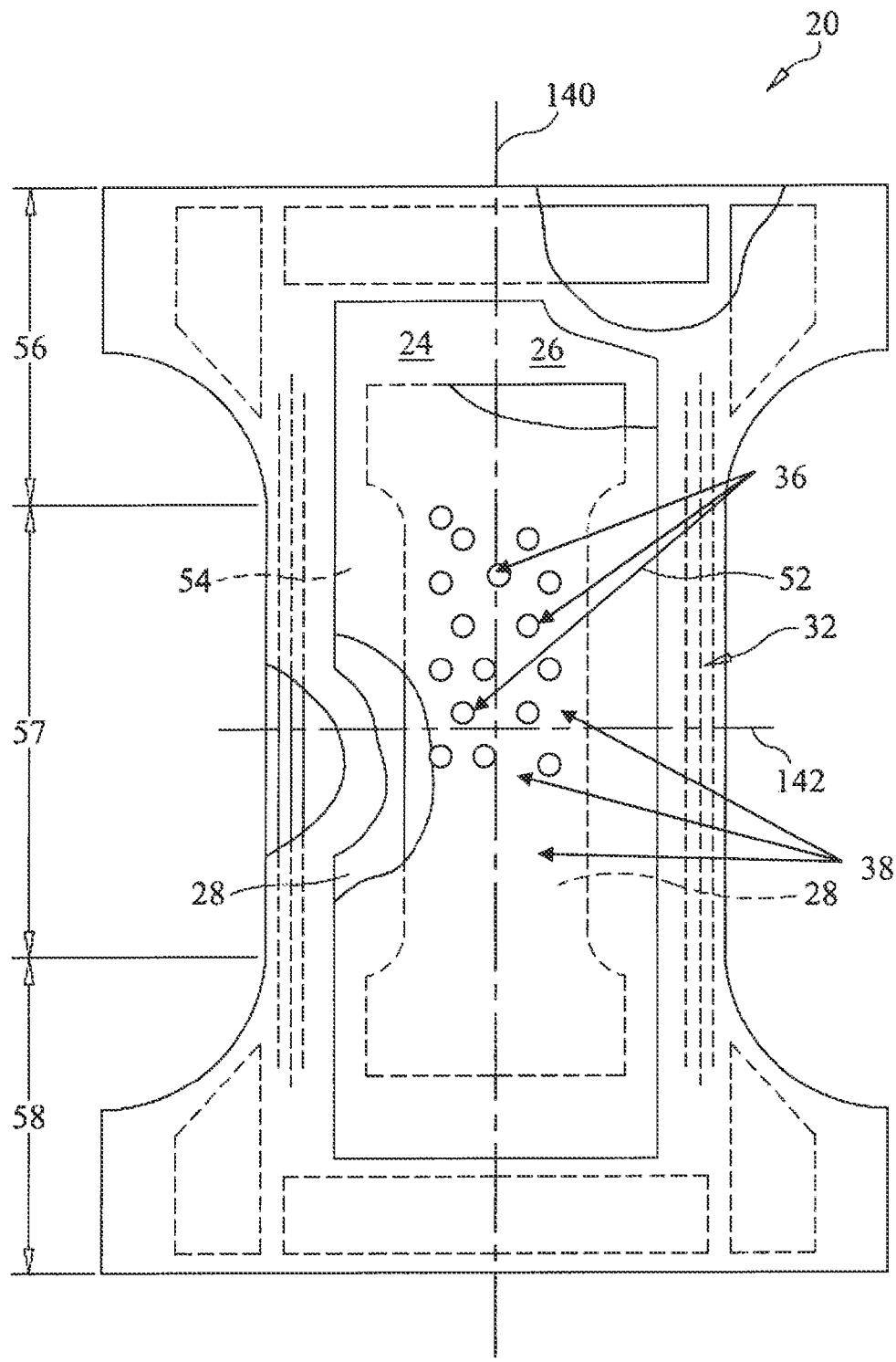
FIG. 1 is a plan view of an absorbent article in accordance with one non-limiting embodiment.

As used herein, the following terms have the following meanings:

Herein, "comprise" and "include" mean that other elements and/or other steps which do not affect the end result can be added. Each of these terms encompasses the terms "consisting of" and "consisting essentially of".

Herein, "body facing surface" refers to surfaces of absorbent articles and/or their component materials which face the body of the wearer, while "garment facing surface" refers to the opposite surfaces of the absorbent articles and/or their component materials that face away from the wearer when the absorbent articles are worn.

Herein, "body" refers to outer layers formed by mammalian epidermal tissues including the skin and hair.

As used herein "absorbent article" refers to devices which are intended to be placed against the skin of a wearer to absorb and contain the various exudates discharged from the body. Absorbent articles of the present invention include diapers, including pant-like diapers, incontinence articles, including e.g. diapers and pads, and feminine hygiene articles, including e.g. sanitary napkins.

As used herein "diaper" refers to an absorbent article generally worn by infants (e.g. babies or toddlers) about the lower torso of the wearer. Suitable diapers are disclosed in, e.g., U.S. Pat. No. 3,860,003 issued to Buell on Jan. 14, 1975; U.S. Pat. No. 5,151,092 issued to Buell et al. on Sep. 29, 1992; U.S. Pat. No. 5,221,274 issued to Buell et al. on Jun. 22, 1993; and U.S. Pat. No. 5,554,145 issued to Roe et al. on Sep. 10, 1996. As used herein the term "diaper" also comprises "pant-like diapers": A pant-like diaper refers to an absorbent article having fixed sides and leg openings. Pant-like diapers are placed in position on the wearer by inserting the wearer's legs into the leg openings and sliding the pant-like diaper into position about the wearer's lower torso. Suitable pant-like diapers are disclosed in, e.g., U.S. Pat. No. 5,246,433, issued to Hasse, et al. on Sep. 21, 1993.

As used herein "incontinence article" refers to an absorbent article worn by a wearer, including pads, undergarments, inserts for absorbent articles, capacity boosters for absorbent articles, briefs, and bed pads. Suitable incontinence articles are disclosed in, e.g., U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and PCT Publication No. WO 92/11830 published by Noel, et al. on Jul. 23, 1992.

As used herein "disposable" is used to describe absorbent articles for single use, which are not intended to be laundered, restored or otherwise reused as an absorbent article after a single use.

The term "longitudinal", as used herein, refers to a line, axis or direction in the plane of the absorbent article that is generally aligned with (e.g., approximately parallel to) a vertical plane which bisects a standing wearer into left and right body halves when the absorbent article is worn. The terms "transverse" or "lateral" as used herein, are interchangeable, and refer to a line, axis or direction which lies within the plane of the absorbent article that is generally perpendicular to the longitudinal direction.

As used herein, the terms "migrate", "migration", or "migrating" mean a lotion composition moves from one place to another place by way of movement on a material or permeation through an (for example intervening) material, within the article.

As used herein, the term "transfer" when used in the context of a lotion composition, refers to the lotion composition moving from one area of the absorbent article to the skin of the wearer or to another area on the absorbent article not by way of migration but by way of direct contact of the skin or said other area with the lotion composition, such as in a blotting effect.

As used herein, the term "particulate material" refers to a component of the lotion composition that is insoluble or non-molecularly dispersible in the lotion composition prior to applying this lotion composition to the absorbent article and that remains in particulate form when applied to the absorbent article. It includes all type of particulate forms such as granules, beads, spheres, micro-spheres, powders, as known in the art.

The terms "reducing the adherence" and "anti-stick" are used synonymously. This means that less residual bowel movement or blood remains on the skin when compared to an article without anti-stick lotion composition and/or that the adherence of feces or menses to the human skin of a wearer wearing an absorbent article is reduced, e.g. compared to adherence of feces or blood observed when an absorbent article without said lotion composition is worn (typically with repeated use).

Herein, the terms "feces" and "bowl movement" and "BM" are used interchangeably. The unit of all molecular weights given herein is Daltons.

The present invention relates to an absorbent article to be worn by a wearer against the skin comprises a backsheet, a skin-contacting sheet, and an absorbent core, said skin-contacting sheet comprising a hydrophilic lotion composition, containing a hydrophilic component and a coloring agent, said lotion composition having a water solubility of at least 30%, typically at least 40%.

In another embodiment, the invention relates to an absorbent article to be worn by a wearer against the skin comprising a backsheet, a skin-contacting sheet and an absorbent core, wherein said skin-contacting sheet comprises a lotion composition comprising i) a first component which is liquid at 25° C.; and ii) a second component which is solid at 25° C., and said first component comprising one or more compounds selected from the group consisting of: a) liquid polyhydric alcoholic solvents; or alternatively, a liquid polyethylene glycol, liquid polypropylene glycol, liquid polyethylene glycol derivatives and/or liquid polypropylene glycol derivatives; and b) liquid fatty acid esters comprising at least one fatty acid unit and at least one (poly) ethylene glycol unit and/or (poly) propylene glycol unit; and said second component comprising one or more compounds selected from the group consisting of (c) solid polyethylene glycols, solid polypropylene glycol, solid polyethylene glycol derivatives and/or solid liquid polypropylene glycol derivatives; (d) solid nonionic surfactants with HLB value of at least 10; (e) solid fatty compounds selected from the group consisting of solid fatty acids, solid fatty soaps and solid fatty alcohols; and (f) ethoxylated natural oils and fats and propoxylated natural oils and fats; whereby said lotion composition comprises (e.g. comprised by said first component and/or said second component comprises) a coloring agent.

The skin-contacting sheet is for example a cuff, and/or a topsheet. The lotion composition may be present in or on part of said sheet, or in or on all of said sheet, for example on part of the sheet, for example as a single stripe, or for example in the form of a pattern, for example including a multitude of stripes.

The coloring agent, or component thereof, may be water-dispersible or oil-dispersible. The coloring agent may comprise a dye component, as described herein. The coloring agent may (also) comprise pigments. The components of the coloring agent may be dissolved and/or dispersed in the lotion composition, e.g. the lotion composition may comprise dispersible, and hence dispersed, colored component(s), including dye particles or pigment particles, and/or soluble and hence dissolved colored component(s), including dissolved dye(s).

The absorbent article may be an infant (e.g. baby, toddler) diaper, or adult incontinence article, like a pad or diaper or feminine hygiene article, like a sanitary pad.

The inventors found that when a colouring agent is incorporated into a hydrophilic lotion composition said colouring agent, or part thereof, may migrate into the article upon wetting (e.g. contact with BM, urine, blood) of the article, even to such an extent that this provides a signal to the user or care taker that the article may need changing.

Said skin-contacting sheet may have one or more first areas comprising said lotion composition and one or more second areas not comprising said lotion composition, and at least one of said first areas having a first color an at least one of said second area having a second, different color, whereby the color difference (ΔE) between said first color of the first area and the second color of the second area may be at least 1.0, at least 2.0, or at least 3.0. It may be that the color difference is as above between each first and second color and/or for each and all of said first and second areas.

Alternatively, the skin-contacting sheet comprising said lotion composition having such a color that it has a ΔE as specified above, compared to a white reference, according to the test method described herein.

Lotion Compositions of the Present Invention

The lotion composition of the present invention is a hydrophilic lotion, which means in one embodiment herein that is has a water solubility of at least 30%, and typically, it may have (an hydrophilicity such that it has) a water solubility of at least 40%, or at least 45% or at least 50%, and optionally up to 65% or up to 60% (as determined according to the method as described herein). In one embodiment herein, the lotion composition is as defined in claim 2, and further described herein after. It may then also have a hydrophilicity and/or water-solubility as specified above.

The lotion composition is present in or on part of the skin-contacting sheet, or in or on all of the skin-contacting sheet, for example the topsheet and/or cuffs. In one embodiment, the absorbent article comprises said lotion composition on part or on all of said topsheet. It may be that the lotion composition is at least, or only, present on the surface of the sheet that in use faces the user, so that it easily transfers to the skin in use. It may be applied to the skin-contacting sheet, e.g. skin-contacting surface thereof, by any means. "Applying" as used herein means that said sheet, or surface thereof or part thereof, comprises at least a partial layer of the lotion composition on at least part of one of its surfaces so that at least part of the lotion composition may contact the skin of the wearer in use.

The lotion composition herein may be flowable (e.g. liquid) at suitable process conditions, e.g. above 50° C. or above 60° C. or above 80° C. or optionally above 100° C., but solid or semi-solid (or non-fluid) at a temperature of 25° C. The lotion composition of the present invention is typically non-fluid, i.e. solid or more often semisolid at 25° C., i.e. at ambient temperatures, to minimize migration of the lotion composition. By "semisolid" is meant that the lotion composition has a rheology typical of pseudoplastic or plastic fluids. When no shear is applied, the lotion compositions can have the appearance of a solid but can be made to flow as the shear rate is increased. In one embodiment herein, this may be due to the fact that while the lotion composition contains a component being solid at 25° C. it also includes a component being liquid at 25° C. (Each component may itself comprise one or more compounds.) The lotion composition may have a final melting point (more than 95% liquid) above potential "stressful" storage conditions that can be 45° C. or greater.

Semi-solid or solid as used herein means that 1 g of a material (e.g. lotion composition, component or compound thereof), which is placed in the middle of a round glass plate having a diameter of 15 cm, does not run off a glass plate within 1 minute, when the glass plate is tilted at 45°, under conditions of 25° C. and 50% relative humidity.

All components or compounds being either solid or semi-solid (according to the test-method described above) are herein referred to as "solid compound or solid component". All components or compounds being not solid or semi-solid (according to the test-method described above) are herein referred to as "liquid compound or liquid component".

In one embodiment, the lotion composition is such that 3% to 90% by weight is a liquid component at test temperature of 25° C. In one embodiment the lotion according to present invention is such that 10% to 80% by weight, or 20% to 75% by weight, or 30% to 60% by weight, or 40% to 50% by weight is liquid at a test temperature of 25° C. From 25% to 75% or even 30% to 80% can be liquid at body temperature of 37° C.

It may be that at 25° C. said solid component is present at a level of from 10 to 97 wt. % of the lotion composition or from 20 to 80 wt. % or from 30 to 70 wt %.

In one embodiment, at 25° C. the total amount of liquid compounds or liquid component is higher than the total amount of solid compounds or component, e.g. the amount of liquid compounds or liquid component is above 50 wt. % or at least 55 wt. % or at least 60 wt. %. When applied to the absorbent article, the lotion compositions of the present invention are transferable to the wearer's skin by normal contact, wearer motion (thus creating friction), and/or body heat.

The lotion composition may comprise a particulate solid coloring agent and, in one embodiment also additional particulate material, as described herein after, which are both for the purpose of the invention then included (e.g. for example for determination of the weight level or ratio's herein) by the solid component (solid at 25° C.).

The amount of lotion composition should typically be such that it effects a reduction of the adherence of feces or menses to the human skin of a wearer wearing an absorbent article compared to the absorbent article without the lotion composition. Without being bound by theory, it is believed that the lotion composition herein may reduce the adhesive force between the soils or exudates and the skin surface because the adhesive forces may be smaller than the cohesive forces within the soils or exudates, thereby allowing the soils or exudates to detach from the skin surface upon application of a shear force (e.g. such as that generated by wiping).

A suitable amount of the lotion composition according to various embodiments of the present invention may be from about 0.015 grams per square meter (gsm) to about 100 gsm, or 1 gsm to about 80 gsm, or 6 gsm to 50 gsm, or 12 gsm to 40 gsm, or 16 to 30 gsm, or for example from 22 to 26 gsm.

Typically, the lotion composition is applied on at least a portion of the topsheet, for example in said amounts described above.

It has surprisingly also been found that it may be beneficial to add particles or beads to the lotion composition, to further reduce the adherence of BM or blood to the skin, in particular particles or beads (other than the coloring agent described herein) that are organic compounds with one or more ester, keton or polyalcohol groups or alkoxylated group(s), such as starch or alkoxylated, e.g. ethoxylated, polyethylene; or inorganic compounds, such as talc, silica, clay, mica seracite. Such beads and properties and quantities thereof are further described below.

Exemplary particles or beads are, as also described in the same section below, polypropylene and/or polyethylene (co) polymer particles and polytetrafluoroethylene particles.

Without being bound by theory, it is believed that the addition of such particles or beads may aid to control the water-solubility and hence hydrophilicity of the lotion such that it provides the reduces adherence to the skin whilst not being so hydrophilic that the lotion dissolves into the bodily exudates, such as urine (and thus to avoid that the lotion may be washed of the absorbent article, or into the article). It has been found that it may be beneficial if the particles or beads have a certain hydrophilicity, whilst not being too hydrophilic.

These particles or beads may be added at any level, for example up to 35% by weight, or up to 20% or up to 15% by weight and for example from 0.1% by weight or from 0.5% by weight, or from 3% by weight or from 5% by weight. Exemplary particle sizes, distributions (etc.) are described in detail below.

In one embodiment, the lotion composition comprises i) a first component which is liquid at 25° C.; and i) a second component which is solid at 25° C., and said first component comprising one or more compounds selected from the group consisting of:

liquid polyhydric alcoholic solvents, liquid polyethylene glycol, liquid polypropylene glycol, liquid polyethylene glycol derivatives, liquid polypropylene glycol derivatives; and liquid nonionic surfactants with HLB value of at least 10; and liquid fatty acid esters comprising at least one fatty acid unit and at least one (poly) ethylene glycol unit and/or (poly) propylene glycol unit;

and said second component comprising one or more compounds selected from the group consisting of
(c) solid polyethylene glycols, solid polypropylene glycol, solid polyethylene glycol derivatives, solid liquid polypropylene glycol derivatives;
(e) solid nonionic surfactants with HLB value of at least 10;
(f) solid fatty compounds selected from the group consisting of solid fatty acids, solid fatty soaps and solid fatty alcohols; and
whereby thus said first component and/or said second component comprises a coloring agent.

The weight ratio of first liquid to second solid component may, for example, be from 1:32 to 9:1 or from 1:9 to 9:1 or from 2:8 to 8:2 or from 3:7 to 7:3.

The lotion composition may be essentially non-aqueous. Non aqueous means, that the lotion compositions either contain no water or they contain water only in minor amounts such as less than 5 wt. % or even less than 1 wt. %. However, these amounts refer to the lotion composition at the time when the absorbent article is produced, i.e. to the time the lotion composition is applied onto the absorbent article. The lotion compositions of the present invention may be hygroscopic, and thus may be able to take up a significant amount of water from the surrounding atmosphere, particularly in an environment with high relative humidity. Thus, when the absorbent article has been stored for a relatively long time, such as for example for unfolded for at least 2 months at 50% relative humidity and 25° C., it is possible that the amount of water contained in the lotion composition has increased to be more than 5 wt %.

In one embodiment herein, the hydrophilic lotion may comprises one or more, or two or more of the following compounds, at least one may be a solid compound and at least one may be liquid compound, in addition to the coloring agent, as described herein.

Liquid Polyhydric Alcoholic Solvents

Liquid polyhydric alcoholic solvents, when used herein, are organic compounds having at least 2 carbon atoms and at least two alcoholic hydroxy groups and which are liquid at 25° C., excluding for the purpose of the invention polyethylene glycols, polypropylene glycols and derivatives, as described herein below, as a separate group. Examples are glycerol, ethylene glycol, diethylene glycol, propylene glycol, butylene glycol, dipropylene glycol, methyl propanediol and derivatives thereof, including for example mono- or di- end capped diethylene glycols, mono- or di-end capped dipropylene glycols, mono- or di-end capped ethylene glycols and mono- or di-end capped propylene glycols, having end-capped units as described above.

Liquid compounds herein may include: ethoxylated fatty acids, such as PEG-8 laurate, available for example as Lipopeg 4-L from Lipo Chemicals; ethoxylated fatty ester (oil), such as a PEG-25 castor oil, for example available as hetoxide C-25 from Global-Seven Inc.; Glycerol esters, such as for example a PEG-10 polyglyceryl-2 laurate, available for example as Hostacerin DGL from Clariant Corp.; Lecithin, such as available as Alcolec BS from American Lecithin Co.; polymeric surfactants such as a C8-C10 alkyl polysaccharide ether, available for example as Glucopan 225 DK from Cognis Corp.); Sorbitan derivatives such as POE (20) sorbitan monopalmitate available for example from Croda Inc.; sucrose and glucose esters and derivatives, such as alkyl polyglucoside, available for example as Simulsol AS48 from Seppic Inc.

Liquid Polyethylene Glycols and Derivatives and Liquid Polypropylene Glycol and Derivatives Liquid polyethylene glycols and derivatives are liquid at 25° C. The polyethylene glycols (PEG's) are made from at least 3 units of ethylene glycol and have the general formula

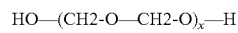

$$HO-(CH2-O-CH2-O)_x-H$$

with x being a number of from 3 to 15 or from 8 to 12. The molecular weight (weight average) may be from 100 to less than 720, or from 100 or 350 to 700. Typical liquid polyethylene glycols are known as PEG-4, PEG-6, PEG-7, PEG-8, PEG-9, PEG-10, PEG-12 and PEG-14. Suitable trade products are for example Polyglykol 400 of Clariant with an average molecular weight of 380 to 410 or Polyglykol 600 with an average molecular weight of 570 to 630.

Liquid PEG and PPG derivatives may include esters and ethers of PEG and PPG. Liquid derivates of PEG and PPG include in particular PEG's and PPG's (for example as described above) having however one or more (mono or di end capped, respectively) end cap groups, derived from an organic compound capable of reacting with a hydroxyl group. End cap groups may include methyl, ethyl, propyl, isopropyl, butyl, isobutyl, tert-butyl and benzyl, for example mono- or di-methyl or- ethyl end capped PEG or PPG. In some embodiment, methyl may be an end-capping unit.

Further polypropylenes and end capping units useful in this invention are described in co-pending application US60/901, 793, filed 16 Feb. 2007.

A liquid mono-end capped PEG is for example a polyethylene glycol monomethyl ether, such as available as Polyglykol M400 from Clariant Corporation. A liquid PEG includes also a polyethylene glycol dimethyl ether with a MW of 500 (available from Sigma Aldrich).

Also useful herein are liquid ethylene oxide-propylene oxide copolymers and polyethylene-polypropylene block copolymers (EO-PO block copolymers), such as Genapol PF10- a EO-PO block copolymer from Clariant Corp.)

Liquid Alkylene (e.g. Ethylene) Glycol Fatty Acid Esters

Suitable liquid alkylene or ethylene glycol fatty acid esters are for example the esters of one or more alkylene glycol units, preferably ethylene glycol units, and one or two fatty acids. Compounds of the present invention may have the general formula $$R^1—(OCH2CH2)_m O—R^2$$

where $R^1$ and $R^2$ are hydrogen or fatty acid residues with e.g. from 6 to 30 or from 8 to 22 carbon atoms and can be the same or different with the proviso that not both are hydrogen; and m is a number of at least 1. $R^1$ and $R^2$ may be different and m may be 1, 2, or 3. Typical ethylene glycol esters are known for example as diethylene glycol diethylhexanoate/diisononanoate, diethylene glycol diisononanoate, diethylene glycol dilaurate, diethylene glycol dioctanoate/diisononanoate and diethylene glycol distearate. Suitable trade product mixtures containing ethylene glycol esters are for example DERMOL MO or DERMOL 489. Wax esters which are liquid at room temperature (25° C.) may be used. They may be derived from natural sources such as jojoba oil, comprising docosenyl eicosenoate, eicosenyl eicosenoate and eicosenyl docosenoate.

Solid Polyethylene Glycol and Polypropylene Glycols and Derivatives Thereof

Solid polyethylene glycols, polypropylene glycols and derivatives thereof are solid (or semi-solid—as defined above) at 25° C., as defined herein. The solid polyethylene glycols are typically made from at least 16 units of ethylene glycol and have the general formula $$HO—(CH2-O—CH2—O)_y—H$$

with y being a number of at least 16, e.g. from 20 to 220 or from 40 to 150. The molecular weight (weight average) is above 720, e.g. from 720 to 100000, or from 950 or 1500 or 2000 or 2700 to 30000. Typical solid polyethylene glycols are known as PEG-20, PEG-32, PEG-40, PEG-45, PEG-55, PEG-60, PEG-75, PEG-90 and PEG-100. Suitable trade products are for example Polyglykol 3000 of Clariant with an average molecular weight of 2700 to 3000 or Polyglykol 4000 with an average molecular weight of 3700 to 4500.

Solid PEG and PPG derivatives may include esters and ether derivates of PEG's and PPG's. Solid derivatives include in particular PEG's and PPG's (for example as described above) having one or more end cap groups (mono or di end capped, respectively), such as those described above.

For example, a solid mono-end capped PEG such as Polyglykol M4000 (polyethylene glycol monomethyl, from Clariant Corporation) may be used and/or a solid di-endcapped PEG such as Polyethylene glycol dimethyl ether MW2000 (from Sigma Aldrich) may be used.

Also useful herein may be solid EO-PO copolymers and EO-PO block copolymers, such as for example Genapol PF80, an EO-PO block copolymer from Clariant Corp.

Solid Nonionic Surfactants

Suitable solid nonionic surfactants with an HLB value of at least 10 include solid PEG derived nonionic surfactants, solid polyalkylene glycol fatty alcohol ethers, such as solid polyethylene glycol fatty alcohol ethers or for example solid polyethoxylated fatty alcohols. The fatty alcohols unit may have from 8 to 30 carbon atoms or from 12 to 22 carbon atoms. The average degree of alkoxylation, e.g. ethoxylation, may be from 2 to 200, at least 10, at least 20 or at least 30. These surfactants may be nonionic surfactants with HLB values of at least 10, or at least 12 or at least 13, up to for example 17. Polyethylene glycol fatty alcohol ethers have the general formula $$R(OCH2CH2)_n OH$$

where R represents an alkyl group or a blend of alkyl groups with for example 8 to 30 or 12 to 22 carbon atoms and n is the degree of ethoxylation, e.g. 2 to 200. Suitable PEG derived surfactants include PEG-12 stearate, PEG-100 stearate, for example available as Tego Acid S 100 P from Evonik/Degussa.

Suitable trade products include also for example BRIJ 76, BRIJ 78 and BRIJ 700 (Steareth 100, available from Croda Inc.).

Other surfactants may include Ceteraeth-10, Ceteareth-20, Polysorbate-65. Also used may be Laureth 23.

Suitable fatty alcohol fatty acid esters are esters of a C10- to C30 fatty alcohol with a C10- to C30-fatty acid. They have the general formula $R^3—CO—O—R^4$ where $R^3—CO$ is a C10- to C30 fatty acid residue and $O—R^4$ is a C10- to C30 fatty alcohol residue. They may be saturated or unsaturated.

Other suitable nonionic surfactant are e.g. ethoxylated alcohols, ethoxylated fatty acids, ethoxylated fatty esters and oils, glycerol esters; sucrose and glucose esters and their derivatives, glucosides, sorbitan derivatives, such as sorbitan monoplamitate.

Other compounds may include PEG oils, like PEG40 hydrogenated caster oil, PEG-20 sorbitan monooleate, PEG-200 castor oil, available for example as Hetoxide C-200 from Global-Seven Inc.; glycerol esters such as a decaglycerol mono/dioleate, available for example as Caprol PGE860 from Abitec Corp.; lecithin derivatives, such as soy phosphatides, such as available as Alcolec Powder from American Lecithin Co.; sorbitan derivatives, such as Polysorbate 65, such as available as Liposorb TS-20 from Lipo Chemicals; sucrose and glucose esters and derivatives such as succinoglycan, available for example as Rheozan from Rhodia, Inc.

Solid Fatty Compounds

The solid fatty compounds are selected from the group consisting of: fatty acids, solid fatty soaps and solid fatty alcohols. The solid fatty compounds are solid at (or at least semi-solid according to the method described herein, at 25° C.). The fatty compounds may have from 10 to 30 or from 12 to 22 carbon atoms. The fatty compounds can be saturated or unsaturated and they can be linear or branched. They may be saturated, linear fatty compounds. Examples of solid fatty acids are decanoic acid, lauric acid, myristic acid, palmitic acid, stearic acid, arachidic acid or behenic acid. Solid fatty alcohols may be linear, unsaturated 1-alkanols with at least 12 carbon atoms. Examples of solid fatty alcohols are lauryl alcohol, myristyl alcohol, cetyl alcohol, stearyl alcohol, arachidyl alcohol or behenyl alcohol.

The solid fatty soaps are metallic soaps which are metal salts of fatty acids. The fatty acid components of the fatty soaps are the same as mentioned above. Suitable metal cations are sodium, potassium, lithium, aluminium, magnesium, calcium, mangan, iron, zirconium, cerium, zinc, cobalt or vanadium. Metallic soaps with low water solubility such as the calcium or magnesium salts, e.g. calcium stearate may be used.

Exemplary Compositions

It may be that the first liquid component comprises one or more compounds selected from the group consisting of: methoxyisopropanol, propyl ether, dipropylene glycol butyl ether, methyl propanediol, propylene carbonate, ethylene glycols, diethylene glycols, propylene glycols, dipropylene glycols, glycerin, sorbitol, hydrogenated starch hydrolysate, silicone glycols, or any of the above mentioned or exemplified polyethylene glycol or derivatives, polypropylene glycol or derivatives, polyethylene glycol derived surfactants, polypropylene derived surfactants, ethylene glycol or derivatives, propylene glycol or derivatives, diethylene glycol or derivatives and dipropylene glycol or derivatives, as described herein.

The second, solid component may comprise for example one or more solid compounds (as defined above) of the group including: solid polyethylene glycol or derivatives thereof; solid polypropylene glycol or derivatives thereof; solid nonionic surfactants with HLB value of at least 10; solid fatty compounds selected from the group consisting of solid fatty acids, solid fatty soaps and solid fatty alcohols; solid PEG derived surfactants; solid PPG derived surfactants; ethoxylated natural fats or propoxylated natural fats, such as PEG-150 jojoba.

Exemplary lotion compositions may be such that:
said first liquid component may comprise a liquid polyethylene glycol and said second component may comprise a solid nonionic surfactant with an HLB value of at least 10, provided that when said solid nonionic surfactant is an alkoxylated (e.g. ethoxylated) fatty alcohol, then the HLB value is at least 13; or
said first component may comprise a liquid fatty acid ester comprising at least one fatty acid unit and at least one ethylene glycol unit and said second component may comprise a solid polyethylene glycol; or
said first component may comprise a liquid polyethylene glycol and said second compound is a solid fatty compounds selected from the group consisting of solid fatty acids and solid fatty soaps and solid fatty alcohols.

When said solid fatty compound comprises a solid fatty acid, then the total amount of liquids is higher than the total amount of solids.

In one embodiment the liquid component is a polyethylene glycol having a molecular weight (weight average) of 100 to less than 720 or from 350 to 700. It may be that the lotion composition comprises from 20% to 80% by weight, or 30% to 70% by weight, or 40% to 60% by weight of this liquid polyethylene glycol. For example 50% by weight of polyethylene glycol with a MW of 400, also referred to as Polyglycol 400.

In one embodiment the solid component is a polyethylene glycol or derivative, where appropriate, having a molecular weight (weight average) of above 720, e.g. from 720 to 100000, or from 950 to 30000, or from 3000 to 20000 or to 10000. It may be that the lotion composition comprises from 20% to 80% by weight, or 30% to 70% by weight, or 40% to 60% by weight of this liquid polyethylene glycol, for example 50% by weight of Polyglycol 4000.

In one embodiment the solid component is a solid nonionic surfactant, including a solid polyethylene glycol fatty alcohol ethers having the general formula

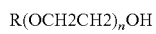

R(OCH2CH2)$_n$OH where R represents an alkyl group or a blend of alkyl groups, with for example 8 to 30 or 12 to 22 carbon atoms, and n is the degree of ethoxylation, e.g. 2 to 200. It may be that the lotion composition comprises from 20% to 80% by weight, or 30% to 70% by weight, or 40% to 60% by weight of this liquid polyethylene glycol, for example 50% by weight of Steareth-100.

Coloring Agent

The lotion composition herein comprises a coloring agent. Surprisingly, when incorporated in the lotion compositions of the invention that are hydrophilic, and/or that comprise the above-described solid and liquid components, the coloring agent migrates into the absorbent article when the article is wetted with bodily exudates, signaling to the user or caretaker that the absorbent article may need changing.

The coloring agent which may be or may comprise a dye component, such as known in the art, but including for example food colorants and food dyes.

In some embodiments, the coloring agent, or components thereof, may be dispersed in the lotion composition. In another embodiment, the coloring agent, or components thereof, may be dissolved in said lotion composition.

The coloring agent, or components thereof, may be water-dispersible or oil-dispersible. The coloring agent may be, or may comprise, a water-soluble dye, such as commonly specified by dye manufacturers.

In one embodiment, the coloring agent comprises dye particles that may be dispersed or dissolved in the lotion composition, or in one embodiment, that may be partially dissolved and partially dispersed in said lotion composition.

In one embodiment herein, the coloring agent comprises pigments, that are present as particulate material, and that may be present in addition to a dissolved dye component, as described herein. For example, the coloring agent may comprise a dissolved dye component and particulate pigments. The pigments may have a different color to the color of the dissolved dye component.

The coloring agent is typically used in amounts sufficient to provide the required coloring of the lotion composition and of the skin-contacting sheet.

The coloring agent may be present in the lotion compositions at a level of for example 0.5 ppm to 5% by weight of the composition, or for example from 1 ppm or 0.005% to 1% or to 0.5% by weight of the composition.

The coloring agent and the lotion composition and the skin-contacting sheet may be such that the color difference (delta E) between an area of the skin-contacting sheet comprising the colored lotion composition and an area of the skin-contacting sheet not comprising the lotion composition is at least 1.0, at least 2.0 or at least 2.2, or at least 2.4 or at least 2.6, or at least 2.8 or at least 3.0, as described in the test method description below. Alternatively, the colored lotion composition-containing skin contacting sheet has a color difference (delta E) compared to a white reference surface of at least 1.0, at least 2.0 or at least 2.2, or at least 2.4 or at least 2.6, or at least 2.8 or at least 3.0, as described in the test method description below. All of the area or areas comprising said lotion composition may have this color difference compared to at least one or all of the area(s) that do not comprising said lotion composition, or compared to a white reference, as described in the test method description below.

The coloring agent may be added to the lotion composition by any known method, including by combining (e.g. mixing) the coloring agent and the remaining lotion composition ingredients, or by for example combining (e.g. mixing) the coloring agent with only one or more of the compounds or components and then combining this with the remaining compounds or components of the lotion composition. For example, the coloring agent may be first combined or dissolved in the liquid component, or compound(s) thereof herein, and then combined with the solid component described herein, or it may be combined with the solid component herein, or compound(s) thereof, and then combined with the liquid component herein.

Exemplary coloring agents include plant-derived dyes.

Examples of coloring agents also include FD&C and D&C dyes, including:
FD&C Blue No. 1 (CI 42090, CAS RN 3844-45-9)
FD&C Yellow No. 5 (CI 19140, CAS RN 1934-21-0)
D&C Yellow No. 7 (CI 45350, CAS RN 2321-07-5)
D&C Green No. 6 (CI 61565, CAS RN 128-80-3)
D&C Green No. 8 (CI 59040, CAS RN 6358-69-6)
FD&C GREEN NO. 3 (C.I. 42053) CAS RN: 2353-45-9
D&C GREEN NO. 5 (C.I. 61570) CAS RN: 4403-90-1

Such dyes are available from for example Sensient Technologies Corporation, 777 East Wisconsin Ave., Milwaukee, Wis. 53202-5304, USA.

Any pigments may be added to the lotion composition, including FD&C and/or D&C pigments, and including plant pigments. It may be that the lotion composition comprises a coloring agent containing a dissolved dye and comprising particulate pigments, said pigments being a different color to the color of the dye(s) (and/or to the color of the coloring agent, excluding said pigments, and/or to the color of the lotion composition, excluding said pigments)).

(Further) Particulate Material

In one embodiment, the lotion composition additionally comprises at least one particulate material for further reducing the adherence of feces or menses to the skin. It should be understood herein that if the coloring agent is present in the form of particles in the lotion composition, then this further particulate material is an additional component. The particulate material includes the particles or beads described above as helping to reduce adherence to the skin of bodily exudates.

The particulate material is particulate during application onto the absorbent article. The particulate material is also such that it remains particulate when in contact with the skin and/or when in contact with urine, menses or feces. Hence, the particulate material is water-insoluble and it has a melting temperature above the processing temperature of the lotion composition, as described above.

The particulate material may have any mean particle size between 1 nanometer to 2 mm, between 1 nanometer to 500 micrometers, between 0.1 micrometer to 2 mm, between 50 nanometers to 1 micrometer, or any range or individual value within any of the ranges set forth herein. The minimum mean particle size may be at least 0.1 micrometer or at least 1 micrometer, or at least 10 micrometers, or at least 20 micrometers, and up to about 500 micrometers or in some embodiments up to about 100 micrometers, and further in other embodiments up to about 30 micrometers. In one embodiment, it may be that the lotion composition to be applied and/or the applied coating comprises particles whereof less than 25% of the particles have an equivalent diameter of greater than 100 microns. In another embodiment, it may be that the lotion composition to be applied and/or the applied coating comprises particles whereof less than 25% of the particles have an equivalent diameter of less than 5 microns. In yet another embodiment, it may be that the lotion composition to be applied and/or the applied coating comprises particles whereof less than 25% of the particles have an equivalent diameter of less than 100 microns.

The particle material may be present in the lotion composition at a level from 0.05% to 25% (by weight of the lotion composition), from 0.05% to 15%, from 0.05% to 5%, or from 0.1% to 25%, or from 0.25% to 20%, but may be from 0.5% to 10% or even up to 5% by weight.

Suitably, the particles may have a density between about 0.5 gram/cm$^3$ and about 2.5 gram/cm$^3$. The density may be between about 0.5 gram/cm$^3$ and about 2.0 gram/cm$^3$, or between 0.8 gram/cm$^3$ and about 1.5 gram/cm$^3$. In one embodiment, the density may be less than about 1 gram/cm$^3$ so as to minimize particle settling and the density is greater than about 0.8 gram/cm$^3$ so as to minimize particle floatation.

In one embodiment, the lotion composition may comprise inorganic particles, including alumina silicates, silicates, silicas, mica and/or talc. Clays may also be used. However, in the present invention it may be that the particulate material is an organic material. The particles may be a non-active and/or non-reactive material. The particles may be porous, or non-porous. The particles may have any shape, and they may have a smooth surface, and they may be spherical or plate-like particles. The particles may comprise a coating agent on their surface or part thereof, for example a surfactant to change its properties, e.g. hydrophilicity. The particles, in particular when they are oleofinic, may include a melt-additive, which is added during the manufacturing of the particles.

Suitable materials include but are not limited to: polystyrene particles, polypropylene and/or polyethylene (co)polymer particles, polytetrafluoroethylene particles, polymethylsilsesquioxane particles, nylon particles. Suitable commercially available particulate materials include but are not limited to: polyethylene particles, available from Honeywell International of Morristown, N.J. under the trade name ACUMIST; polymethyl methacrylate particles (microspheres), available from KOBO of South Plainfield, N.J. as BPA; lactone cross polymer particles (microspheres), available from KOBO as BPD; nylon 12 particles (microspheres), available from KOBO as NYLON SP; polymethylsilsesquioxane particles (microspheres), available from KOBO as TOSPEARL; cellulose particles (microspheres), available from KOBO as CELLO-BEADS; polytetrafluoroethylene powders, available from Micro Powders, Inc. of Tarrytown, N.Y. as MICROSLIP; blends of natural wax and micronized polymers as are available form Micro Powders as MICROCARE and particles of a copolymer of vinylidene chloride, acrylonitrile and methylmethacrylate available as EXPANCEL from Expancel, Inc. of Duluth, Ga. Micronized waxes, such as are available from Micro Powders as MICROEASE may also be incorporated. Polyolefin particles (powders) as are available from Equistar Chemical Corp. Houston, Tex. as MICROTHENE may be used. MICROTHENE FN510-00 from Equistar may be used.

Skin-Contacting Sheet

The absorbent article herein comprises at least on skin-contacting sheet comprising the lotion composition. This skin-contacting sheet may be any sheet of the absorbent article that in use contacts the skin.

The skin-contacting sheet may comprise over its entire surface said lotion composition, or only on a portion or portions thereof. Typically, at least a total surface area (measured on the surface facing the user in use) of at least 1 cm$^2$, at least 4 cm$^2$ or in some embodiments even at least 10 cm$^2$ or at least 15 cm$^2$ comprises said lotion composition with the coloring agent; and thus the skin-contacting sheet may comprise said lotion composition such that the total area of said sheet with lotion composition thereon or therein is at least 1 cm$^2$, at least 4 cm or at least 10 cm$^2$ or at least 15 cm$^2$, or for example at least 30 cm$^2$ or at least 50 cm$^2$, and in certain embodiments for example at least 70 cm$^2$ and for example up to 100 cm$^2$.

The lotion composition may be present on only a portion of the skin-contacting sheet. Then, as illustrated in FIG. 1, the skin-contacting sheet comprises areas 36 with said lotion composition and areas 38 without said lotion composition, forming thus said pattern. The area with the lotion composition may be in any form, including a square or rectangular shape, e.g. stripe, and it may for example be present in the area facing the genitals and/or anus, e.g. center ⅓ of the article; or the lotion composition may be present in a pattern, i.e. a pattern of areas with the lotion composition, including rectangular shapes like stripes, square shapes, circular or oval shapes, or even figurative figures.

The pattern in which the lotion composition may be applied or the amount of lotion composition applied can be the same for the rear third of the article (i.e. a third of the longitudinal extension of the absorbent articles starting from the outer edge of the chassis in the rear waist region), the central third of the article and the front third of the article.

Alternatively, the pattern, in which the lotion composition is applied and/or the amount of lotion composition applied can be different for the rear, central and front third of the article. As the lotion composition of the present invention has anti-stick properties, it may be comprised in those regions of the absorbent articles, which lie adjacent the skin areas of the wearer, which typically are contaminated with blood or feces. Thus, the lotion composition should at least be comprised in those regions of the articles, which lie adjacent the buttocks and the whole groove length of the wearer in use, and/or in the region of the genitals.

If the lotion composition is applied in the form of longitudinal stripes, the stripes may extend into the rear waist region of the absorbent article to the extent that they also cover the buttocks and most of the groove length. Also, the number or the density of the stripes may be higher in those areas lying against the areas typically affected with feces smeared against the skin, e.g. the back half of the article. Further, the basis weight of the stripes may be higher in those areas lying against the areas typically affected with feces smeared against the skin. If the lotion composition is applied in the form of figures, like dots, the density of the figures (e.g. dots density, dots being closer together) and/or the size of the figures and/or the basis weight of the lotion composition comprised by the figures may be higher in those areas lying against the areas typically affected with feces smeared against the skin. The figures can have any shape and size such as round, oval, rectangular, triangular, star-shaped, heart-shaped or shaped in the form of an animal. Also, the absorbent article can comprise different shapes and/or different sizes.

The skin-contacting sheet may be a cuff or part thereof of the article, and typically two cuffs are at least present and the article may thus comprises at least two of such skin-contacting sheets.

These cuffs may be a pair of leg cuffs or a pair of barrier cuffs, or both pairs may be present. A barrier cuff or leg cuff is typically attached to said absorbent article with one longitudinal edge of said cuff, thus having a free longitudinal edge that can be positioned out of the X-Y plane (longitudinal/transverse directions) of the article, i.e. in z-direction. The cuffs of a pair are typically mirror images of one another in the Y-axis of the article.

In one embodiment a part or all of the cuff or cuffs may comprise the hydrophilic lotion composition described herein. In one embodiment herein, said cuff comprises said lotion composition on less then 80% of the cuff material, or less then 60%, or less then 40%, or even less then 20%, but at least 10%.

In one embodiment, the skin-contacting sheet is the topsheet or part thereof of the article. The topsheet may be any sheet known in the art as topsheet, including so-called bodyside liners, core coversheets, or genital coversheets, and/or an anal and/or vaginal cuff, sometimes also referred to as topsheet with one or more openings to receive bodily exudates (e.g. large openings, e.g. of at least 2 cm$^2$ or at least 4 cm$^2$, to receive bodily exudates). For example, U.S. Patent Application No. 2006/0058766 A filed on Sep. 13, 2005 discloses an absorbent article wherein the topsheet is provided with at least one opening adapted to receive fecal material, the topsheet and the opening thereof each having a front region and a back region. A void space between the absorbent core and the topsheet is provided and the absorbent article further comprises a genital coversheet, which in use covers the genitals, and which is positioned in, under or above said front region of the opening. Either said topsheet, or said genital coversheet, or both may comprise the lotion composition herein.

In one embodiment, the exposure of the skin-contacting sheet to bodily exudates should be maximized, and the skin-contacting sheet is therefore the topsheet or part thereof, of the article.

Materials for the skin-contacting sheet may include woven sheets, nonwoven sheets, and films, including laminates thereof, and/or including apertured nonwovens and apertured films and apertured formed films, and including apertured formed thermoplastic films, apertured plastic films, and hydroformed thermoplastic films; but also including porous foams; reticulated foams; reticulated thermoplastic films; and thermoplastic scrims. Suitable woven and nonwoven materials can be made of natural fibers (e.g., wood or cotton fibers), synthetic fibers (e.g., polymeric fibers such as polyester, polypropylene, or polyethylene fibers) or from a combination of natural and synthetic fibers.

Skin-contacting sheets that are or made of material(s) that are compliant, soft feeling, and non-irritating to the wearer's skin may be used. Further, the skin-contacting sheet may be liquid pervious permitting liquids (e.g., urine) to readily penetrate through its thickness, allowing thus the migration of the coloring agent from the sheet into the article upon contact with bodily exudates.

The topsheet may be made of an apertured sheet, having a plurality of apertures having an aperture size of at least about 0.2 mm$^2$, but less than 2 cm$^2$, or less than 1 cm$^2$, or less than 0.5 cm$^2$. Such an apertured sheet may have an open area of at least about 10%, the open area being the sum of the surface area of all apertures, on the surface faces the user in use.

Further suitable skin-contacting sheets are disclosed e.g. in U.S. Patent Application No. 2004/0092902 A; U.S. Patent Application No. 2004/0092900 A; U.S. Patent Application No. 2004/0162538 A; and U.S. Patent Application No. 2006/0058765 A.

Absorbent Articles

This invention refers to any absorbent articles such as such as diapers, adult incontinence articles, and feminine hygiene articles. These articles comprise for the purpose of the invention a skin-contacting sheet comprising the lotion composition herein. This skin-contacting sheet may be the topsheet and/or the cuffs of the article, if present.

Each of these articles typically comprises, in addition to the skin-contacting sheet, a backsheet and an absorbent core and a topsheet, if this is not the skin-contacting sheet herein. The absorbent core may comprise a core-cover sheet and one or more absorbent structures and/or absorbent materials therein. It may be that the topsheet and/or the backsheet form the absorbent core covers, optionally combined with a further covering sheet, and then the absorbent core comprises one or more absorbent materials enclosed by that the backsheet and or topsheet and optionally additional covering sheet. Alternatively, the absorbent core cover sheet or sheets are in addition to the topsheet and/or backsheet.

In the following, a diaper is illustrated as one embodiment of an absorbent article. However, as the skilled person is aware of, most of the components and materials described herein below are also applicable to other absorbent articles. FIG. 1 is a plan view of a diaper 20 in accordance with one non-limiting embodiment. The diaper 20 has portions cut away to reveal the underlying structure, the surface which will form the outer surface of the disposable garment is facing away from the viewer.

An absorbent article herein (such as diaper 20) may have a longitudinal axis 140 and a transverse axis 142. The diaper 20 has further an inner, body facing surface 52 and an outer, garment facing surface 54 opposed to the inner surface.

One end portion of the diaper 20 is configured as a front waist region 56 of the diaper. The opposite end portion is configured as a back waist region 58 of the diaper 20. An intermediate portion 57 of the diaper 20 is configured as a crotch region, which extends longitudinally between the front and back waist regions. The crotch region 57 is that portion of the diaper which, when the diaper is worn, is generally positioned between the wearer's legs.

The chassis of the diaper comprises the main body of the diaper 20. The chassis comprises typically a liquid pervious topsheet 24, e.g., as described above, and a backsheet 26. The chassis further includes an absorbent core 28 positioned between the topsheet 24 and the backsheet 26, optionally enclosed by a core cover material/sheet(s). The chassis has a periphery which is defined by the transverse outer edges of the chassis with longitudinal edges and end edges.

Typically, the absorbent article comprises one or more cuffs 32, that may be the skin-contacting sheet or sheets herein, said cuffs 32 extending in longitudinal direction along the longitudinal side edges of the absorbent article, or part thereof.

The backsheet 26 may typically be a liquid impervious backsheet, as known in the art. In one embodiment, the liquid impervious backsheet comprises a thin plastic film such as a thermoplastic film having a thickness of about 0.01 mm to about 0.05 mm. Suitable backsheet materials comprise typically breathable material, which permit vapors to escape from the absorbent article while still preventing exudates from passing through the backsheet 26. Suitable backsheet films include those manufactured by Tredegar Industries Inc. of Terre Haute, Ind. and sold under the trade names X15306, X10962 and X10964. The backsheet, or any portion thereof, may be elastically extendable in one or more directions.

The backsheet 26 may be directly or indirectly attached to or joined with for example the topsheet 24 herein and/or the barrier and/or leg cuffs 32 herein.

The absorbent core 28 generally is disposed between the topsheet 24 and the backsheet 26. The absorbent core 28 may comprise any absorbent material that is generally compressible, conformable, non-irritating to the wearer's skin, and capable of absorbing and retaining liquids such as urine and other certain body exudates.

The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulosic fibers, tissue including tissue wraps and tissue laminates, absorbent foams, absorbent sponges, superabsorbent polymers, absorbent gelling materials, or any equivalent material or combinations of materials. The configuration and construction of the absorbent core may also be varied, e.g. the absorbent core may have varying caliper zones, a hydrophilic gradient, a superabsorbent gradient, or lower average density and lower average basis weight acquisition zones; or may comprise one or more layers or structures. The total absorbent capacity of the absorbent core should, however, be compatible with the design loading and the intended use of the diaper. Further, the size and absorbent capacity of the absorbent core may be varied to accommodate wearers ranging from infants through adults.

Further, the diapers herein may comprise a front and back waist band 34 and/or a fastening system, typically joined to the waistband, as known in the art. Fastening systems may comprise fastening tabs and landing zones, wherein the fastening tabs are attached or joined to the back region 58 of the diaper and the landing zones are part of the front region 56 of the diaper. A pants-type diaper may not have such fasteners, but it may have a back waist band and front waist and that are joined to form a continuous waistband.

Test Methods

Water Solubility

Water solubility of the lotion composition or any compound used to formulate the lotion composition is determined as follows: 100 mg starting amount (SA) of the lotion composition is applied to a glass slide (2.5 cm×8 cm) of known weight, such that the lotion covers an area of 2.5 cm×5 cm on the glass slide. The slide is then placed flat in a beaker containing 75 ml of deionized water at 20° C. The water with the lotion composition therein is not stirred. After 4 hours the glass slide is removed from the beaker and put in an oven at 60° C., 0% RH (relative humidity) to remove the water. After drying it is weighted to determine the residual amount of lotion composition on the slide. The lotion composition of the present invention is water soluble if residual amount (RA) of lotion composition on the plate after drying is below 60%, below 20% or below 10% (of the 100 mg that have been applied to the glass slide). These values correspond to a water solubility of at least 40%, at least 80% or at least 90% which is determined as follows:

$$[(SA-RA)]/SA \times 100\% = \text{water solubility (in \%)}$$

Such lotion compositions having relatively good water solubility are considered to be hydrophilic within the meaning of the present invention.

Color Differentiation Method

The color differences and color intensities as used herein are measurable as follows.

A tristimulus color meter (spectrophotomer/colourimeter), such as a HunterLab Labscan XE operated under Universal Software 4.1 (available from Hunter Associates Laboratory Inc., Reston Va.), is to be used, with the following settings/configurations:

Colour Scale: CIE L*a*b*; Illumination: C; Standard Observer: 2°; Geometry: 45/0°;

Port Diameter: 0.2 inch; Viewing Area Diameter: 0.125 inch; UV Filter: Nominal.

The instrument is calibrated according to the vendor instructions using the standard black and white tiles provided by the vendor. Calibration should be performed before each set of analyses, to determine a value herein.

Measurements are done on the article as a whole, or on a sample taken there from, if necessary, and they are done on the surface of the skin-facing sheet that comprises the colored lotion composition, e.g. the surface that faces the user in use.

If the skin contacting sheet comprises areas with said colored lotion composition and areas without said colored lotion composition, then the color difference between such two areas can be determined via a paired measurement. Then, the paired measurements are performed such that one measurement is done on an area comprising the colored lotion, and one measurement is done on an area not comprising said lotion composition.

If the color intensity is to be determined with respect to a white reference, a paired measurement can be done, whereby one measurement is performed on the colored lotion containing skin-contacting sheet, and one measurement is done on the white reference tile provided with the equipment.

The sample is placed flat with respect to the colorimeter's measurement port. A selected sample area (see below) is placed over the port, making certain the port is completely covered by this area. Then, the white standard tile is placed on the opposing surface of the article's area that is being measured, centered over the instrument port for use as a uniform backing. Readings are taken for L* a* b* and recorded to 0.01 units. Then, the second measurement of the paired measurement is done (place the white standard tile on the opposing surface of the measured area, as before, if applicable). Again readings are taken for L* a* b* and record to 0.01 units.

At least three paired measures should be performed in each lotioned area, or non-lotioned area, to obtain an average value, that is reported herein: e.g. if the lotioned area is a stripe over the length of the article, then a measurement can be done in the front third of the article, the middle third, and the back third of the article where lotion is present.

Differences between the paired measurements are calculated using the following standard equation:

$$\Delta E=[(L^*_{lotion}-L^*_{non-lotion})^2+(a^*_{lotion}-a^*_{non-lotion})^2+(b^*_{lotion}-b^*_{non-lotion})^2]^{0.5}$$

Or:

$$\Delta E=[(L^*_{lotion}-L^*_{white\ reference})^2+(a^*_{lotion}-a^*_{white\ reference})^2+(b^*_{lotion}-b^*_{white\ reference})^2]^{0.5}$$

Then, the other two $\Delta E$'s of the other two paired measurements is calculated and an average $\Delta E$ of the three paired measurements is reported to 0.1 units. This is the $\Delta E$ used herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article to be worn by a wearer against the skin comprising a backsheet, a skin-contactable sheet, and an absorbent core, the skin-contactable sheet comprising a hydrophilic lotion composition, the hydrophilic lotion composition having a water solubility of at least 30%, wherein the hydrophilic lotion composition comprises:
    25% to 75% by weight of a first component which is liquid at 25° C., the first component comprising one or more compounds selected from the group consisting of liquid nonionic surfactants having an HLB value greater than or equal to 10, liquid polyhydric alcoholic solvents, and liquid fatty acid esters comprising at least one fatty acid unit and at least one (poly) ethylene glycol unit and/or (poly) propylene glycol unit;
    25% to 75% by weight of a second component which is solid at 25° C., the second component comprising one or more compounds selected from the group consisting of solid polypropylene glycols, solid polypropylene glycol derivatives, solid ethoxylated natural oils, solid ethoxylated natural fats, solid propoxylated natural oils, and solid propoxylated natural fats; and
    a coloring agent comprising a dissolved, water-soluble dye.

2. An absorbent article to be worn by a wearer against the skin comprising a backsheet, a skin-contactable sheet and an absorbent core, wherein the skin-contactable sheet comprises a lotion composition comprising i) 25% to 75% by weight of a first component which is liquid at 25° C.; and ii) 25% to 75% by weight of a second component which is solid at 25° C., wherein:
    the first component comprises one or more compounds selected from the group consisting of liquid nonionic surfactants having an HLB value greater than or equal to 10, liquid fatty acid esters comprising at least one fatty acid unit and at least one (poly) ethylene glycol unit, and liquid fatty acid esters comprising at least one fatty acid unit and at least one (poly) propylene glycol unit; and
    the second component comprises one or more compounds selected from the group consisting of
    (a) solid polyethylene glycols, solid polypropylene glycol, solid polyethylene glycol derivatives and/or solid polypropylene glycol derivatives;
    (b) solid nonionic surfactants with HLB value of at least 10;
    (c) solid fatty compounds selected from the group consisting of solid fatty acids, solid fatty soaps and solid fatty alcohols; and
    (d) ethoxylated natural oils and fats and propoxylated natural oils and fats; wherein the first component and/or the second component comprises a coloring agent, the coloring agent comprising a dissolved, water-soluble dye.

3. The absorbent article of claim 2, wherein the lotion composition has a water solubility of at least 40%.

4. The absorbent article of claim 2 wherein the first component comprises a liquid fatty acid ester comprising at least one fatty acid unit and at least one ethylene glycol unit and the second component comprises a solid polypropylene glycol.

5. The absorbent article of claim 1, wherein the skin-contactable sheet is a topsheet of the article.

6. The absorbent article of claim 1, wherein the coloring agent comprises particulate pigments.

7. The absorbent article of claim 1, wherein the lotion composition is applied to the skin-contactable sheet in an amount of at least 12 gsm.

8. The absorbent article of claim 1, wherein the skin-contactable sheet has one or more first areas comprising the lotion composition and one or more second areas not comprising the lotion composition, and at least one of the first areas having a first color and at least one of the second area having a second different color, wherein the color difference (ΔE) between the first color of the first area and the second color of the second area is at least 1.0.

9. The absorbent article of claim 1, wherein the coloring agent comprises one or more of FD&C dyes, D&C dyes, and pigments.

10. The absorbent article of claim 1, wherein the lotion composition comprises a polyethylene glycol or polyethylene glycol derivative selected from the group consisting of a) a solid polyethylene glycol, a solid polyethylene glycol derivate, a liquid polyethylene glycol, and a liquid polyethylene glycol derivative.

11. The absorbent article of claim 1, wherein the absorbent article is one of an incontinence article, feminine hygiene article, or infant diaper.

* * * * *